US009804107B2

(12) United States Patent
Sugiyama et al.

(10) Patent No.: US 9,804,107 B2
(45) Date of Patent: Oct. 31, 2017

(54) PATTERN MEASUREMENT DEVICE AND COMPUTER PROGRAM FOR EVALUATING PATTERNS BASED ON CENTROIDS OF THE PATTERNS

(71) Applicant: Hitachi High-Technologies Corporation, Minato-ku, Tokyo (JP)

(72) Inventors: Akiyuki Sugiyama, Tokyo (JP); Miki Isawa, Tokyo (JP); Satoru Yamaguchi, Tokyo (JP); Motonobu Hommi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/103,894

(22) PCT Filed: Nov. 17, 2014

(86) PCT No.: PCT/JP2014/080287
§ 371 (c)(1),
(2) Date: Jun. 13, 2016

(87) PCT Pub. No.: WO2015/098349
PCT Pub. Date: Jul. 2, 2015

(65) Prior Publication Data
US 2016/0313266 A1   Oct. 27, 2016

(30) Foreign Application Priority Data

Dec. 27, 2013   (JP) .................................. 2013-270811

(51) Int. Cl.
*G01N 23/00*   (2006.01)
*G01N 23/22*   (2006.01)
(Continued)

(52) U.S. Cl.
CPC ......... *G01N 23/2206* (2013.01); *G01B 15/00* (2013.01); *G01N 23/2251* (2013.01);
(Continued)

(58) Field of Classification Search
CPC ..... G01N 23/00; G01N 23/2251; H01J 37/00; H01J 37/02; H01J 37/302; H01J 37/3023;
(Continued)

(56) References Cited

U.S. PATENT DOCUMENTS

| 8,398,868 B2 | 3/2013 | Cheng et al. | |
|---|---|---|---|
| 2008/0073528 A1* | 3/2008 | Sasaki | H01J 37/265 250/307 |

(Continued)

FOREIGN PATENT DOCUMENTS

| JP | 2011-233210 A | 11/2011 |
|---|---|---|
| JP | 2012-22907 A | 2/2012 |

(Continued)

OTHER PUBLICATIONS

International Search Report (PCT/ISA/210) issued in PCT Application No. PCT/JP2014/080287 dated Mar. 3, 2015 with English translation (3 pages).

(Continued)

*Primary Examiner* — Jason McCormack
(74) *Attorney, Agent, or Firm* — Crowell & Moring LLP

(57) ABSTRACT

The purpose of the present invention is to provide a pattern measurement device for quantitatively evaluating a pattern formed using a directed self-assembly (DSA) method with high accuracy. The present invention is a pattern measurement device for measuring distances between patterns formed in a sample, wherein the centroids of a plurality of patterns included in an image are determined; the inter-centroid distances, and the like, of the plurality of centroids are determined; and on the basis of the inter-centroid dis- (Continued)

tances, and the like, of the plurality of centroids, a pattern meeting a specific condition is distinguished from patterns different from the pattern meeting the specific condition or information is calculated about the number of the patterns meeting the specific condition, the size of an area including the patterns meeting the specific condition, and the number of imaginary lines between the patterns meeting the specific condition.

11 Claims, 13 Drawing Sheets

(51) Int. Cl.
    *G01B 15/00*     (2006.01)
    *G03F 7/00*     (2006.01)
    *G01N 23/225*     (2006.01)

(52) U.S. Cl.
    CPC ........ *G03F 7/0002* (2013.01); *G01B 2210/56* (2013.01); *G01N 2223/071* (2013.01); *G01N 2223/6116* (2013.01)

(58) Field of Classification Search
    CPC ...... H01J 37/3026; H01J 37/304; H01J 37/26; H01J 37/261
    USPC ........................... 250/306, 307, 311; 382/144
    See application file for complete search history.

(56) References Cited

U.S. PATENT DOCUMENTS

| | | | | |
|---|---|---|---|---|
| 2009/0242760 A1* | 10/2009 | Miyamoto | ......... | G01N 23/2251 250/307 |
| 2011/0267718 A1 | 11/2011 | Itakura et al. | | |
| 2013/0105690 A1 | 5/2013 | Katou et al. | | |
| 2015/0136976 A1* | 5/2015 | Matsuoka | ............. | H01J 37/222 250/306 |

FOREIGN PATENT DOCUMENTS

| | | | |
|---|---|---|---|
| JP | 2012-98240 A | | 5/2012 |
| JP | 2012098240 A | * | 5/2012 |
| JP | 2012-527752 A | | 11/2012 |

OTHER PUBLICATIONS

Japanese-language Written Opinion (PCT/ISA/237) issued in PCT Application No. PCT/JP2014/080287 dated Mar. 3, 2015 (3 pages).

* cited by examiner

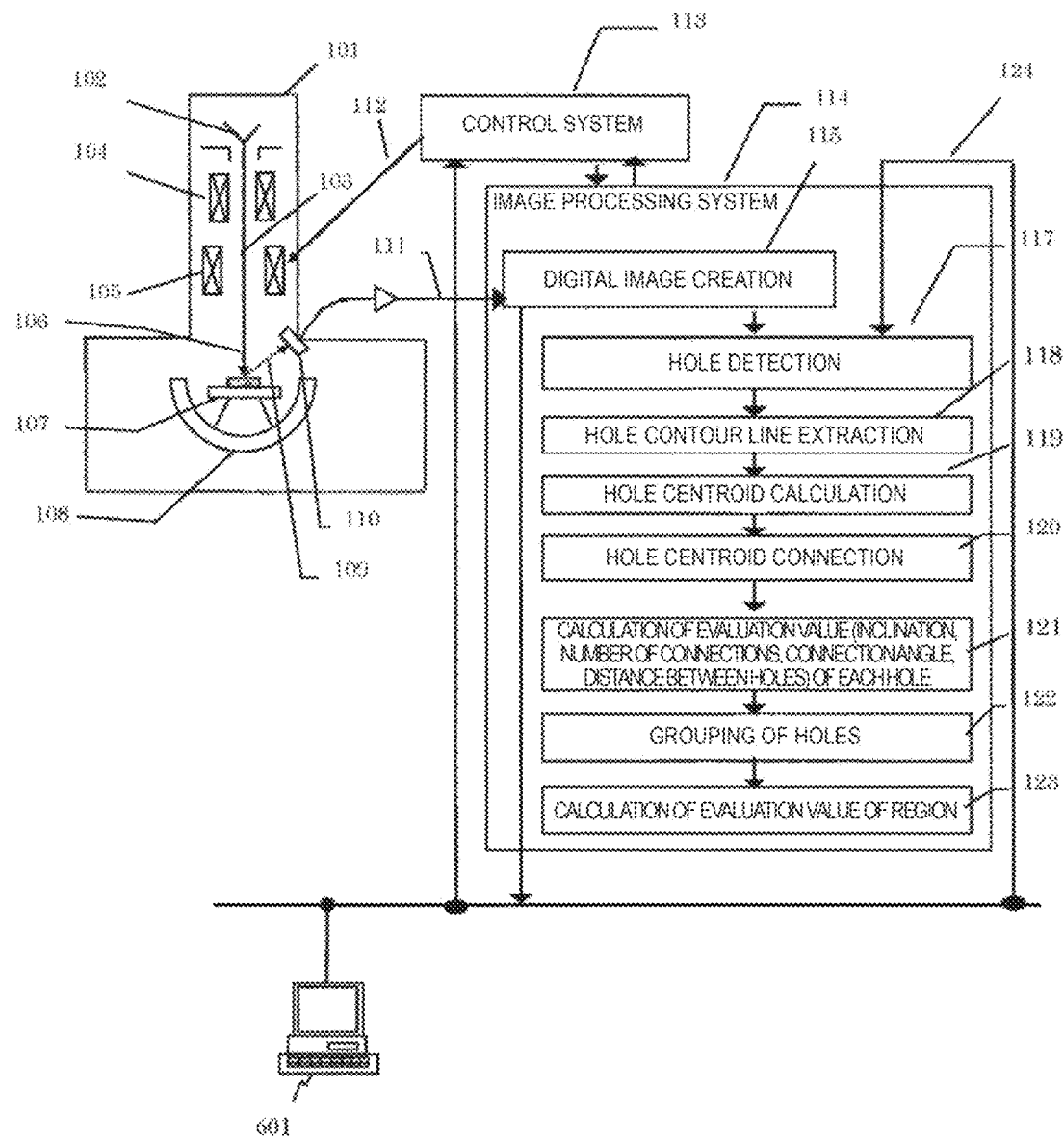
[Fig. 1]

[Fig. 2]
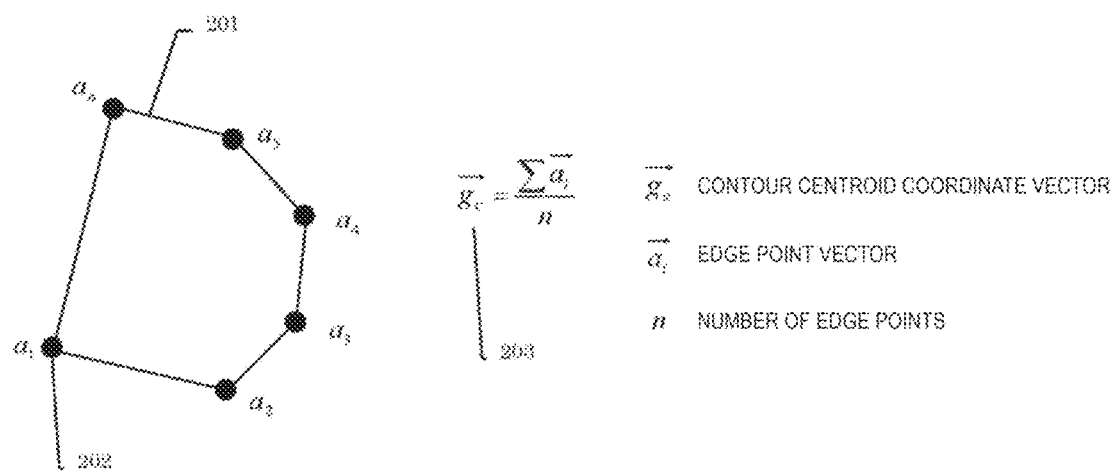
[Fig. 3]
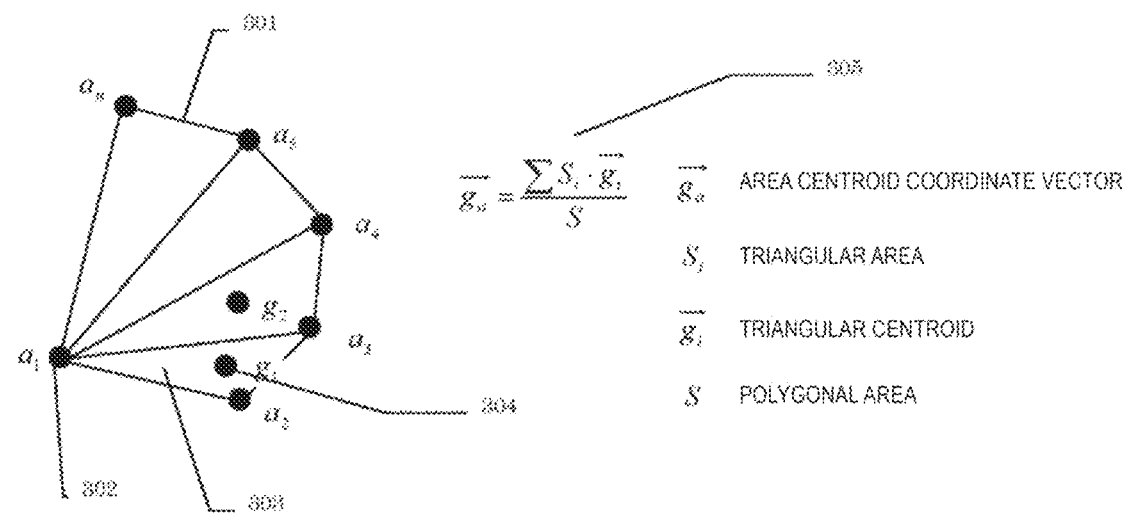

[Fig. 4]
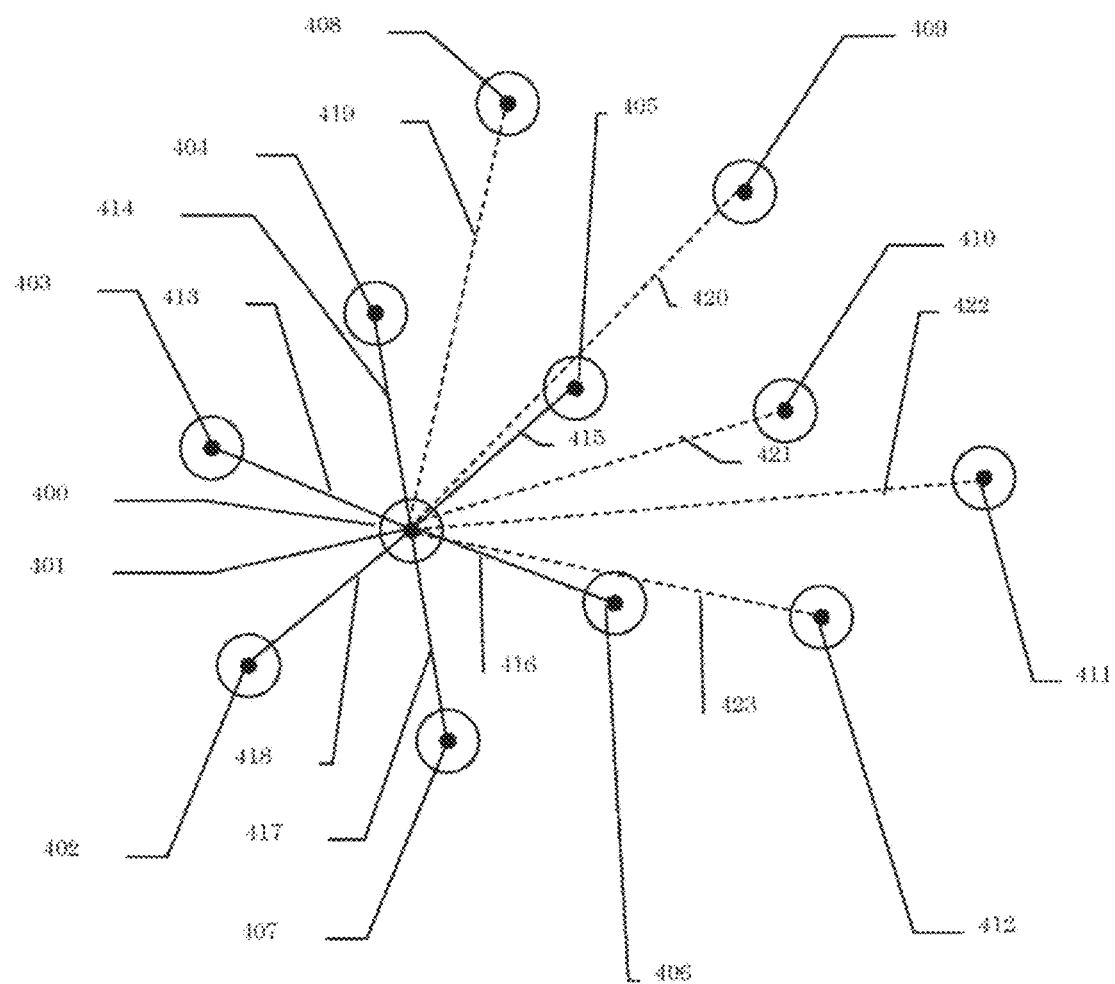

[Fig. 5]
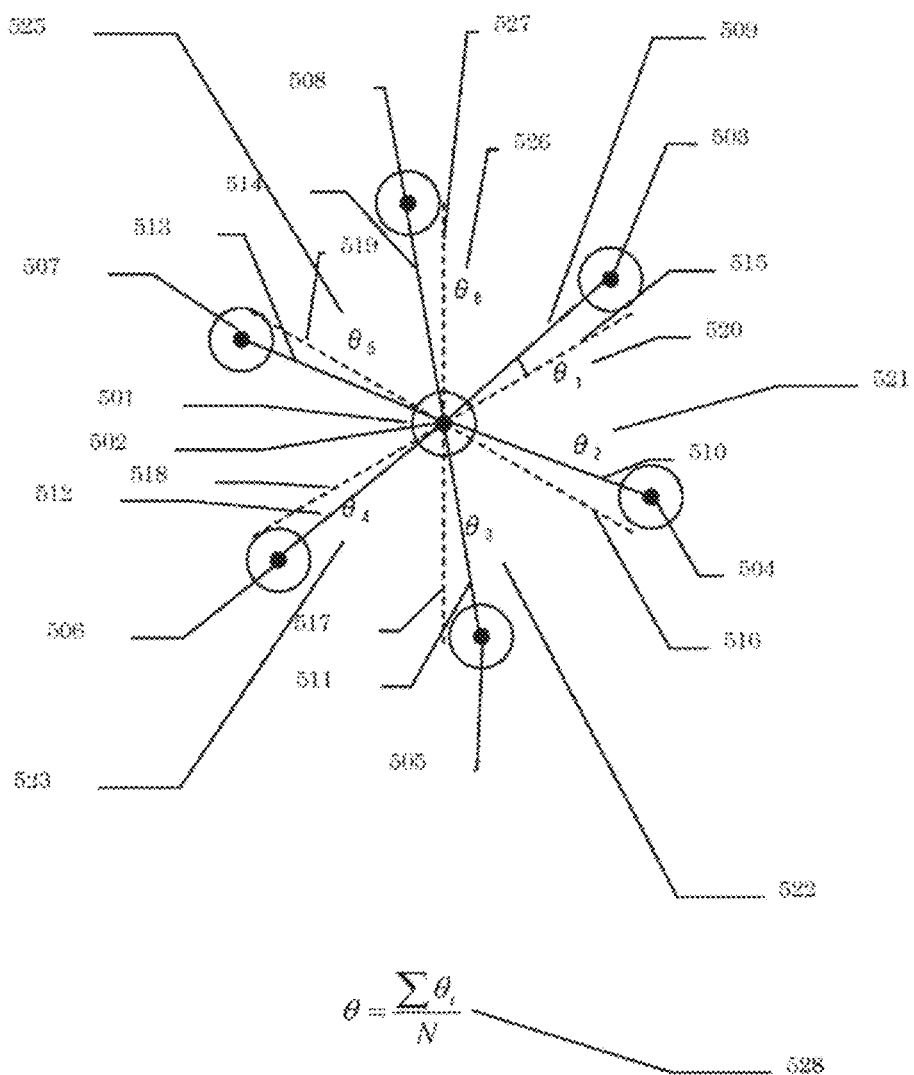

[Fig. 6]
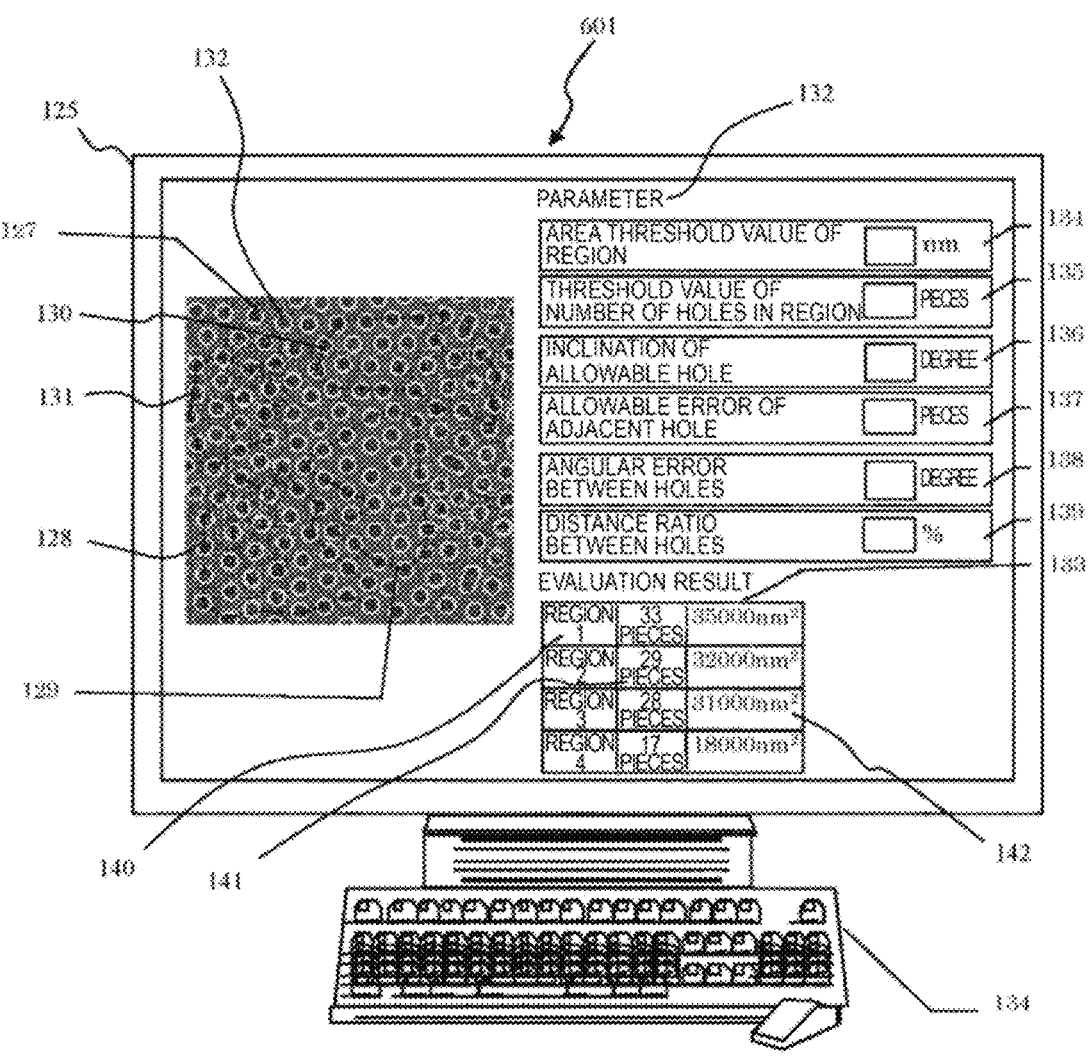

[Fig. 7]

```
AMP(FCR for Hole)
Object
        Data
        ☐ Number (Total)
        ☐ Number (Normal Hole)
        ☐ Number (Defect Hole)
        ☐ Average (Diameter)
        ☐ 3Sigma (Diameter)
        ☐ Average (Pitch)
        ☐ 3Sigma (Pitch)
        ☐ Average (Roundness)
        ☐ 3Sigma (Roundness)

Design Value       Pitch (nm)     [ 38 ]  nm
                   Diameter (nm)  [ 16 ]  nm
```

[Fig. 8]

```
AMP Customize(FCR for Hole)
    Threshold ▼ Auto
              [ Specify ]
              ☐ Gray Level            [ 50 ]  %  (0~100%)
              ☐ Pitch Search Area     [  0 ]  %  ±30%
              ☐ Diameter Search Area  [  0 ]  %  ±10%
              ☐ Roundness             [ 0.7]     (0.5~1.0)
```

[Fig. 9]

| AMP (FCR for Grain Area) | | |
|---|---|---|
| Object | ☐ Data ☐ Number (Total) ☐ Number (Normal Hole) ☐ Number (Defect Hole) ☐ Number (Grain Area) ☐ Average (Hole Number) ☐ Maximum (Hole Number) ☐ Average (Pitch) ☐ 3Sigma (Pitch) | |
| Design Value | Pitch (nm) 36 Diameter (nm) 16 | nm nm |

[Fig. 10]

| AMP Customize(FCR for Grain Area) | | |
|---|---|---|
| Threshold ▼ Auto / Specify | | |
| ☐ Gray Level | 50 | % (0~100%) |
| ☐ Pitch Search Area | 0 | % (±30%) |
| ☐ Hole Number | 100 | % (90~110%) |
| ☐ Minimum Grain Number | 10 | (5~) |

[Fig. 11]
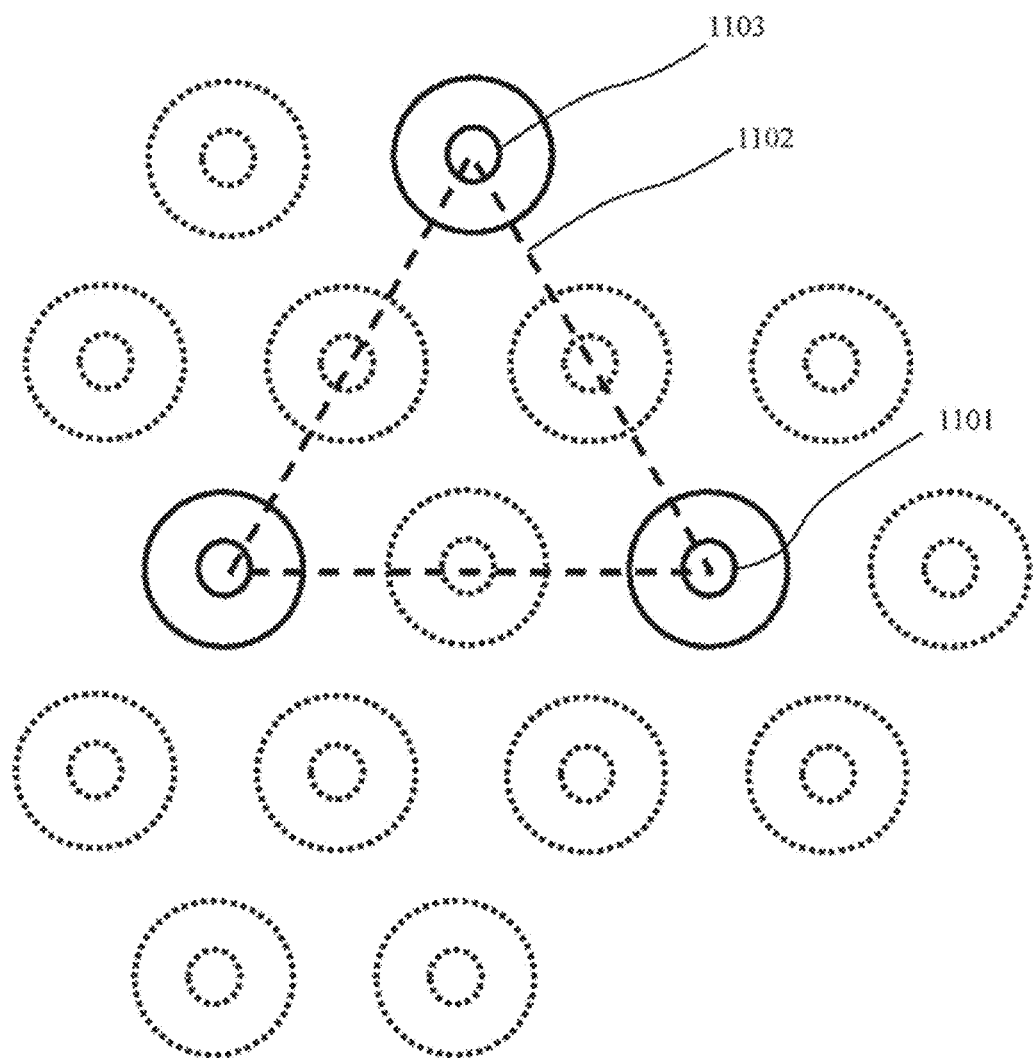

[Fig. 12]
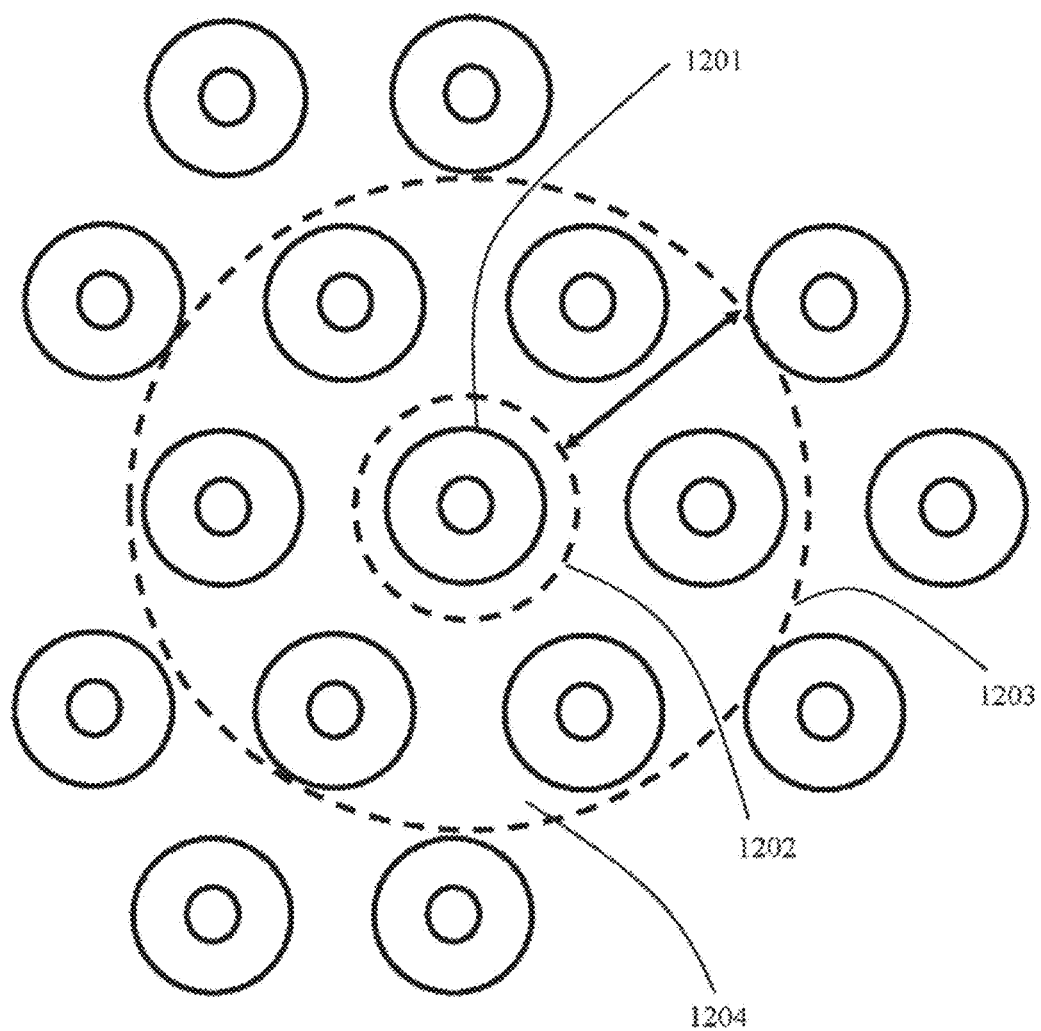

[Fig. 14]
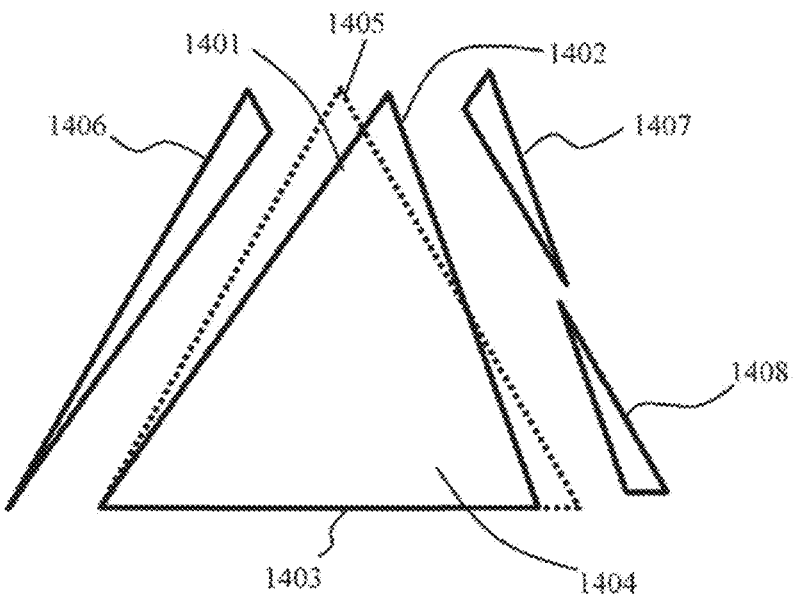
[Fig. 15]
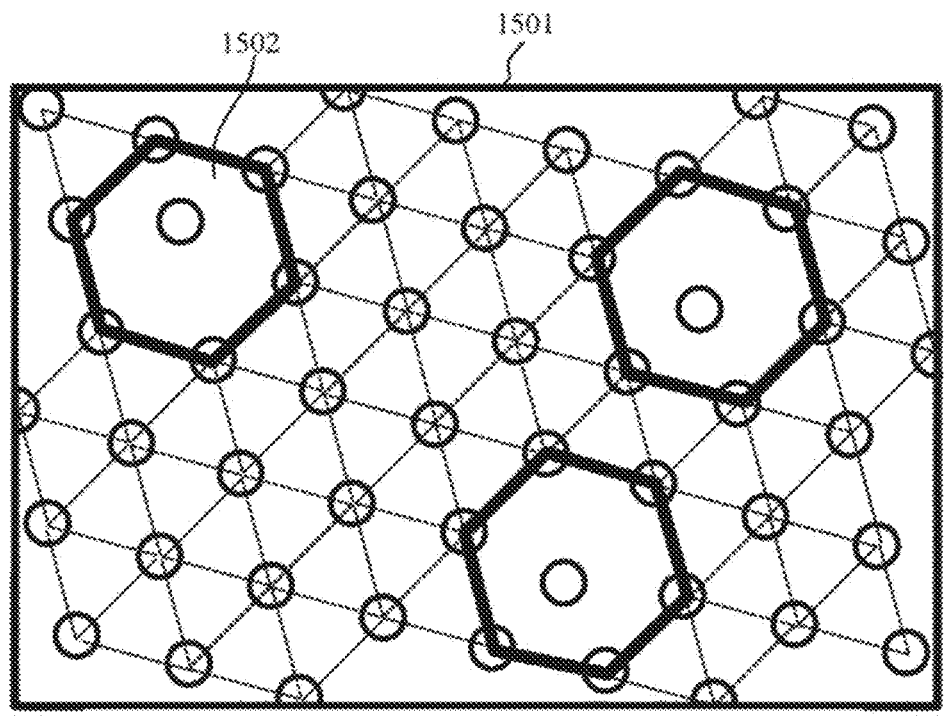

[Fig. 16]
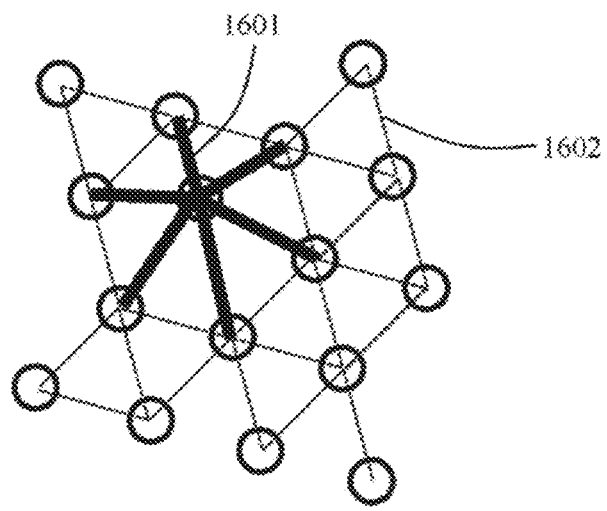
[Fig. 17]
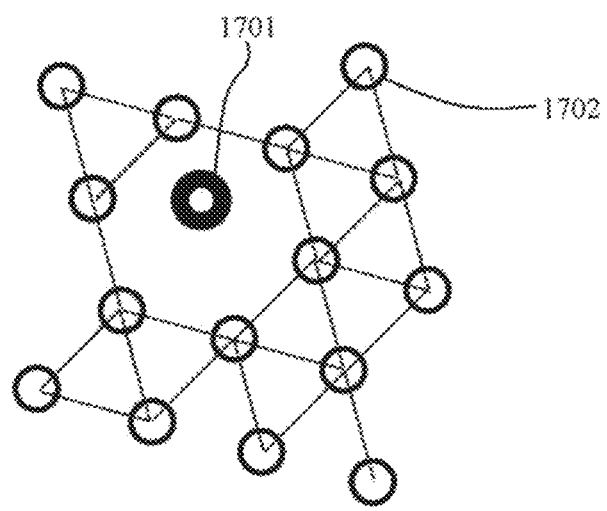

[Fig. 18]
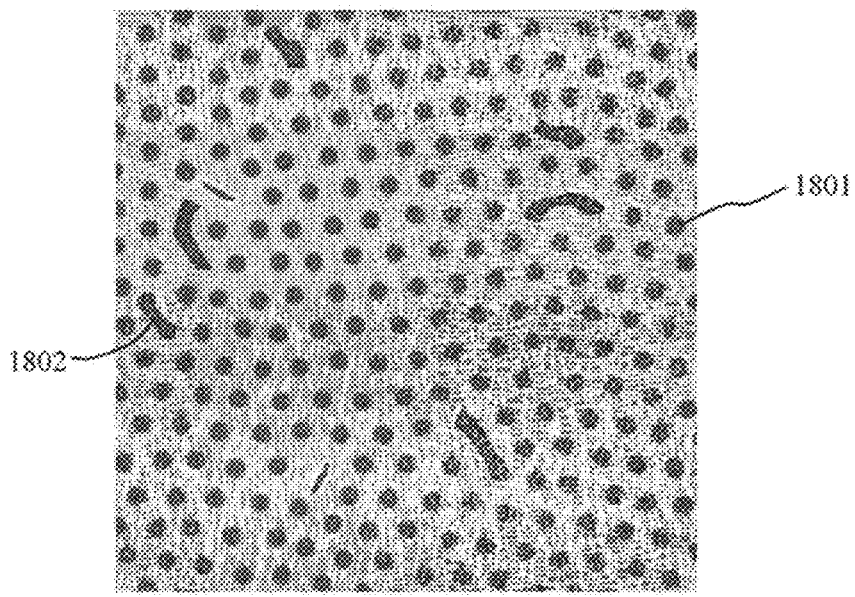
[Fig. 19]
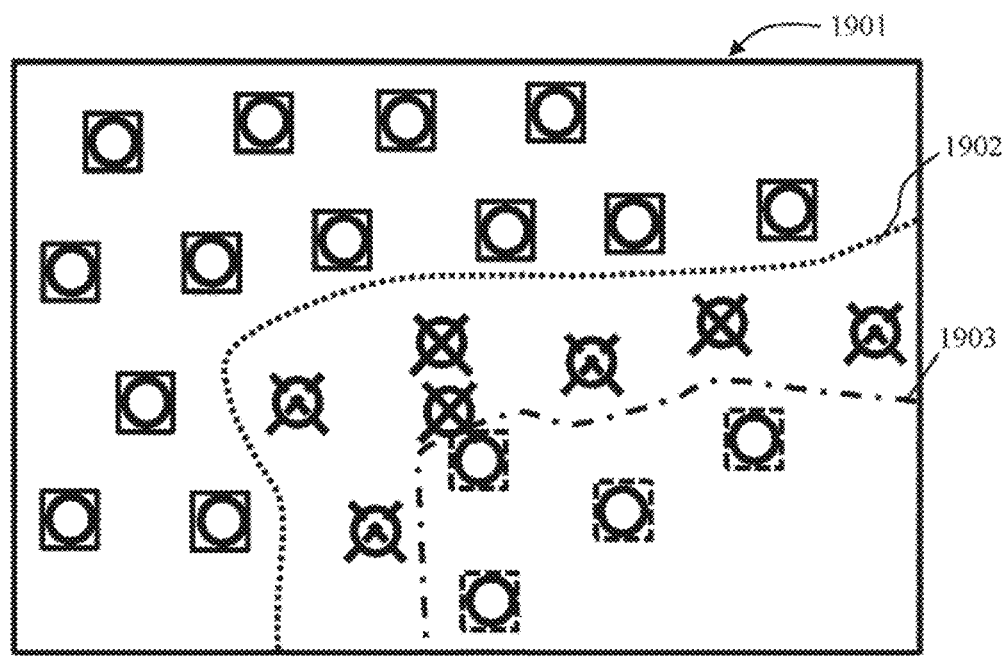

PATTERN MEASUREMENT DEVICE AND COMPUTER PROGRAM FOR EVALUATING PATTERNS BASED ON CENTROIDS OF THE PATTERNS

TECHNICAL FIELD

The present invention relates to a pattern measurement device and a computer program causing a computer to measure a pattern, particularly, to the pattern measurement device and the computer program which are appropriate for evaluating a self-assembly pattern.

BACKGROUND ART

Formation of a circuit shape is difficult as a circuit becomes fine in a semiconductor manufacture. In the related art, the circuit shape is formed by an exposing technology. However, there are resolution limitations of a laser beam used in exposure, and even when an exposing technology such as liquid immersion exposure and multiple exposure, which improves the resolution limitations is used, formation of the circuit shape is difficult.

For example, in international Roadmap for Semiconductors 2012 which is a roadmap of a semiconductor manufacture, regarding a DRAM, manufacturing of a pattern having 14.2 nm at a ½ pitch in 2019 has been planned, and regarding an MPU/ASIC Metal 1, manufacturing of a pattern having 13.4 nm at a ½ pitch in 2019 has been planned. Formation of a circuit shape having the above dimensions only using a general patterning technology is difficult. For this reason, researchers of the semiconductor manufacture field examine a forming technology using self-assembly of molecules, which is referred to as Directed Self-Assembly (below abbreviated to DSA).

In the DSA technology, polymer is used as a material in which self-assembly is performed. If a silicon wafer is coated with the polymer and is heated, a shape in which multiple holes are opened, or a shape in which a line may be formed so as to be layer-like is formed by self-assembly. In this case, because simply using the multiple holes or a layer-like line in a circuit is not possible, a guide pattern for controlling self-assembly is formed so as to be loose, and a space in the guide pattern is densely filled by self-assembly.

PTL 1 discloses an example in which individual separation domains are slantingly arranged in patterning of using the DSA method.

CITATION LIST

Patent Literature

PTL 1: JP-T-2012-527752 (corresponding U.S. Pat. No. 8,398,868)

SUMMARY OF INVENTION

Technical Problem

In the USA technology, evaluation of polymer is important. However, neither of an item for evaluating a shape which is obtained in such a manner that polymer is heated so as to perform self-assembly, nor a method of quantitatively converting the evaluation into a numerical value are not clearly disclosed.

In a circuit forming technology (DSA) using self-assembly of polymer, which is a micro-processing technology for manufacturing a semiconductor, evaluation of a self-assembled shape is required. Particularly, in material evaluation of polymer, necessity for evaluating a range in which alignment is performed by self-assembly may occur in the future. PTL 1 does not disclose a technique of quantitatively evaluating patterns which are regularly arranged.

In the following descriptions, a pattern measurement device and a computer program which have a purpose for quantitatively evaluating patterns formed by a DSA method, with high accuracy are proposed.

Solution to Problem

As an aspect for achieving the abovementioned purpose, there is provided a pattern measurement device which includes a calculation device and a computer program of causing the computer to perform the following measurement. The calculation device measures dimensions between patterns formed on a sample, by using data which is obtained by irradiating the sample with a beam. The calculation device obtains centroids of a plurality of patterns contained in the data, obtains at least one of an inter-centroid distance of the plurality of patterns, angle information of imaginary lines which link the plurality of centroids to each other, and area information of a closed shape formed by the imaginary lines, distinguishes at least one of a pattern which meets a specific condition, an area including the pattern which meets the specific condition, and an imaginary line between patterns meeting the specific condition, from at least one of a pattern different from the pattern which meets the specific condition, an area other than the area including the pattern which meets the specific condition, and an imaginary line between patterns other than the patterns meeting the specific condition, on the basis of at least one of the inter-centroid distance, the angle information, and the area information which have been obtained, or computes information regarding at least one of the number of patterns meeting the specific condition, a size of the area including the patterns which meet the specific condition, and the number of imaginary lines between patterns meeting specific condition.

Advantageous Effects of Invention

According to the configuration, it is possible to quantitatively evaluate a pattern formed by a DSA method, with high accuracy.

BRIEF DESCRIPTION OF DRAWINGS

FIG. 1 is a diagram illustrating an example of a semiconductor measurement device (pattern measurement device).

FIG. 2 is a diagram illustrating an example of a calculation method of a hole centroid.

FIG. 3 is a diagram illustrating an example of a calculation method of the hole centroid.

FIG. 4 is a diagram illustrating an example of a method for hole centroids.

FIG. 5 is a diagram illustrating an example of an inclination calculation method of the hole centroid.

FIG. 6 is a diagram illustrating an example of a Graphical User Interface (GUI) for a measurement parameter, which is displayed on a display screen of an input device.

FIG. 7 is a diagram illustrating an example of the display screen on which a measurement result of a pattern formed by a DSA method is displayed.

FIG. 8 is a diagram illustrating an example of a details setting screen for the measurement parameter.

FIG. 9 is a diagram illustrating an example of the display screen on which the measurement result of the pattern formed by the DSA method is displayed.

FIG. 10 is a diagram illustrating an example of a details setting screen for the measurement parameter.

FIG. 11 is a diagram illustrating an example in which an imaginary line is set between centroids of patterns separated from each other.

FIG. 12 is a diagram illustrating a technique of selecting a pattern which is positioned from a reference pattern at a specific distance.

FIG. 14 is a diagram illustrating a technique of obtaining area information of a closed shape formed by an imaginary line which is set between centroids.

FIG. 15 is a diagram illustrating an example in which an area in which arrangement conditions of a pattern do not satisfy predetermined conditions is distinguished from other areas, and is displayed.

FIG. 16 is a diagram illustrating an example in which an imaginary line in which an inter-centroid distance of patterns does not satisfy predetermined conditions is distinguished from other imaginary lines, and is displayed.

FIG. 17 is a diagram illustrating an example in which a pattern in which an inter-centroid distance of patterns does not satisfy predetermined conditions is distinguished from other patterns, and is displayed.

FIG. 18 is a diagram illustrating an example in which distinguishment information in accordance with features of a pattern is superimposed on a DSA pattern image having high magnification.

FIG. 19 is a diagram illustrating an example in which distinguishment information in accordance with features of a pattern is superimposed on a DSA pattern image having low magnification.

DESCRIPTION OF EMBODIMENTS

Figure 13A:
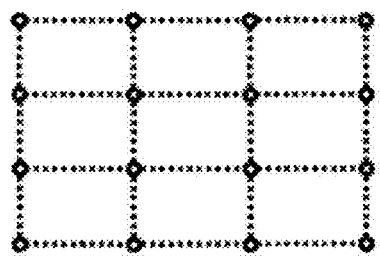
FIGS. 13A-13C are diagrams a diagram illustrating an arrangement example of the pattern formed by the DSA method.

Examples which will be described below relate to a method and a device of evaluating a shape of a hole or a dot (pattern) in a case where polymer forms a shape by self-assembly in a DSA technology, so as to form the hole or the dot. In the examples which will be described below, capturing is mainly performed by using an electron microscope, and automatic evaluation is performed by image processing for an electron microscope image. With the image processing, specifying a self-assembly area and evaluating the self-assembly area are automatically performed.

When a material of polymer is evaluated, it is desired that a range aligned by the self-assembly is evaluated. In a general measurement method, conversion into a numerical value and examination are difficult. In the examples which will be described below, a device for quantitatively converting the range aligned by the self-assembly into a numerical value, a computer program for causing a computer to perform quantification, and a storage medium for storing the computer program will be described.

In a case where patterns (for example, hole patterns) formed by the self-assembly of polymer are clearly aligned, a regular hexagon is formed by an imaginary straight line which links centroids of the formed patterns to each other, and a honeycomb structure in which regular hexagons are filled in a plane is formed. The center of the hole corresponds to the center of the regular hexagon. Thus, the number of holes adjacent to each hole is six. Polymer in which, as described above, regular hexagons are appropriately formed over a range is referred to as a polymer appropriate for patterning with the DSA method. That is, when polymer is created or when the quality of the polymer is managed, it is evaluated whether or not such hexagons are appropriately formed over a wide range, and thus it is possible to improve the quality of the polymer itself, or to maintain the quality. The manufacturer of a semiconductor device performs the above-described evaluation, and thus can achieve improvement or maintaining of yield of semiconductor devices.

EXAMPLE 1

In the example, an example of a device of evaluating a shape of polymer subjected to the self-assembly will be described. FIG. 1 is a diagram illustrating an example of a semiconductor measurement system which includes a pattern measurement device. In an electron microscope 101, electron beams 103 emitted from an electron gun 102 are condensed by an electron lens 104, and a sample 106 is irradiated with the condensed electron beams. The irradiation with the electron beams causes secondary electrons 109 and reflection electrons to be generated from the surface of the sample 106. A degree of secondary electrons generated by collision of the secondary electrons 109 and reflection electrons and/or electrons emitted from the sample with other members is detected by an electron detector 110. A deflector 105 is controlled by a control signal 112 of a control system 113 so as to one-dimensionally or two-dimensionally scan the sample 103 with the electron beams 103. The size of a field of view (FOV) of the electron microscope may be controlled by the control signal 112. A probe diameter of the electron beams 103 with which the sample 103 is irradiated may be controlled by amplitude of an exciting current which is supplied to an objective lens (not illustrated). An SEM image obtained by scanning with the electron beam 103 is displayed in a calculation device 601. FIG. 6 is an enlarged view of the calculation device 601 which includes a display device 125. An aspect ratio of an electron microscope image 127 displayed in the display device 125 is equal to a ratio between a scanning range with the electron beam 103 in an X direction and a scanning range in a Y direction.

A sample stage 107 may cause a sample stage control device 108 to move a sample 106 with respect to the electron beam 103. A signal 111 output from the electron detector 110 is subjected to AD conversion in an image processing system 114. A digital image creation unit 115 forms an electron microscope image 127 on the basis of a digital signal. A calculation device (processor) for performing calculation processing as will be described later is mounted in the image processing system 114. The calculation device extracts a waveform signal or a contour line of a pattern, on the basis of the obtained SEM image. The calculation device performs dimension measurement processing for a pattern or a space between patterns, by using the waveform signal or contour line data. Such dimension measurement processing and the like may be performed with a computer program stored in the calculation device 601.

The display device 125 is a device that displays an electron microscope image 127. Information input by an operation device 134, measurement results obtained on the basis of the input information, or the like is displayed in the display device 125.

The control system 113 controls the electron microscope 101 on the basis of coordinate information functioning as a measurement target on a sample, or optical condition information. The control system 113 controls the electron microscope 101 and the like on the basis of information input from the calculation device 601 or information transferred from the image processing system 114. The control system 113 transfers device condition information and the like of the electron microscope 110 to the image processing system 114. The components illustrated in FIG. 1 are connected to each other through communication means, and necessary information is transferred between the components.

The calculation device included in the image processing system 114 performs calculation processing as will be described below. A hole detection unit 117 detects a hole contained in an electron microscope image which has been created by the digital image creation unit 115. The hole is detected, for example, in such a manner that a template (for example, image in which one hole pattern is displayed) in which a hole pattern is displayed is stored in a storage medium and the like which are mounted in the image processing system 114, in advance, and searching is performed on an SEM image by using the template. In this case, for example, normalized correlation processing is performed, and thus it is possible to extract an image area which is the same as the template or is approximate to the template. Because polymer obtained by combining two types of materials is subjected to annealing, and thus a plurality of patterns which has a hole shape is arranged on a sample, multiple holes are contained in an electron microscope image 127 of the sample, and it is possible to detect an image area of the multiple holes by the normalized correlation processing.

Then, a hole contour line extraction unit 118 extracts a contour line of an edge portion of a hole, from an image area of each hole which is detected by the hole detection unit 117. As a method of extracting a contour line from an electron microscope image of a hole, for example, a method of performing calculation from a line profile obtained by integrating a plurality of pixels from the center of a hole, a method of performing calculation by using a differential filter with respect to an electron microscope image and binarizing the image, and the like are provided. In addition to the binarization, waveform profiles are formed in a direction perpendicular to edges extracted by the binarization, and peak positions and the like thereof are connected to each other. Thus, it is possible to form a contour line with high accuracy by extracting a contour line.

Then, a hole centroid calculation unit 119 calculates centroid coordinates of each hole from contour line data obtained by the hole contour line extraction unit 118. As a method of calculating the centroid of a hole from a contour line of the hole, a plurality of methods is provided. Examples of the plurality of methods include a method of performing calculation by using an area inside the contour line; and a method of averaging coordinates of hole contour lines. In addition, coordinates calculated by the hole detection unit 117 may be used as they are. Though any method is used, the hole centroid coordinates can be calculated. A difference in accuracy of the coordinates is present, but the result can be obtained.

Then, a hole centroid connection unit 119 performs processing of connecting centroid coordinates of holes detected by the hole contour line extraction unit 118, to each other. As a method of connecting, firstly, distances between the calculated multiple hole centroid coordinates are calculated. The number of holes adjacent to each hole when holes are clearly aligned as described above is 6. The number of holes adjacent to each hole when holes are not clearly aligned is at most about 8. Thus, if about 8 holes are selected in order of a short distance, by using distances between centroid coordinates of holes, and holes having values of the distances which are close to each other are selected again, a relationship between holes which are necessarily adjacent to each other is specified. If the method of specifying adjacent holes is applied to all of the calculated holes, all of the adjacent holes are connected to each other.

As illustrated in FIG. 12, centroid coordinates included in an area 1204 which are from a first predetermined value 1202 to a second predetermined value 1203 with respect to a centroid position of a predetermined reference pattern 1201 may be extracted, and thus an adjacent hole pattern may be recognized.

Parameters for determining whether or not an adjacent hole is formed at an appropriate position may be set on a GUI screen as illustrated in FIG. 6. For example, the number of holes adjacent to one hole may be set in the setting area 137. As described above, in a case where holes are clearly aligned, the number of adjacent holes is 6. In a case where holes are not clearly aligned, the number of adjacent holes is 5 obtained by subtracting 1, or 7 obtained by adding 1. For example, if a setting value in the setting area 137 is set to "6", an area formed by imaginary lines linking the holes to each other may be recognized as an area in which patterns are not appropriately arranged, in a case where the number of adjacent holes is 5 or in a case where the number of adjacent holes is 7. In addition, a hole which has the adjacent holes of 5 or less, or a hole which has the adjacent holes of 7 or more may be recognized as a pattern which is not formed at an appropriate position (is not appropriately aligned). Since a hole pattern in which the number of adjacent patterns is 6 is a pattern which is appropriately formed, for example, in order to be distinguished from a pattern which is not appropriately formed, 6 adjacent hole patterns are connected to a hole pattern at the center by imaginary lines, and a result of connection is displayed. Thus, it is possible to figure out a distribution state indicating whether or not appropriate formation is performed. If the setting value in the setting area 137 is set to "5 to 7", in a case where the number of adjacent patterns is from 5 to 7, it is recognized that an area in which patterns are appropriately arranged, these patterns, or an interval between these patterns is provided. The area, the pattern, or an imaginary line of connecting the patterns to each other is distinguished from other areas, other patterns, or other imaginary lines of connecting patterns to each other. A pattern and the like which do not satisfy a predetermined condition may be distinguished from other patterns, and may be displayed. Further, a plurality of threshold values may be set.

In a setting area 138, an angular error between holes may be set. In a setting area 139, a distance ratio between holes may be set. In a case where holes are clearly aligned, the number of adjacent holes is set to 6, and a relative angle of a first imaginary line between hole centroids, and a second imaginary line which is adjacent to the first imaginary line is set to 60 degrees. Because, if centroids are connected to each other, a regular triangle is ideally formed, each relative angle between two adjacent imaginary lines is set to 60 degrees. For example, if the setting value in the setting area 138 is set to be "58 to 62", a pattern, an imaginary line, an area, and the like which have a relative angle of 57 degrees or less and 63 degrees or more are determined to be normal. Information thereof is stored in a predetermined storage medium or is displayed in the display device.

In a case where holes are clearly aligned, distances between holes are equal to each other. Actually, all of the distances are not equal to each other, but it is considered that the distances are converged so as to have an error of about 10%. For example, when a value of "10" is set in the setting area 139, if a distance ratio between adjacent imaginary lines is more than 10%, the holes are determined to be holes which are not clearly aligned, and it is considered that the imaginary line is not appropriately connected.

In a case where holes which are clearly aligned are multiple, a distance having a high frequency among distances between holes may be considered as a reference inter-hole centroid distance. For example, in a case where a value of "20" is designated in the setting area 139, in a case where a distance is less than 80% of the reference inter-hole centroid distance and is more than 120% thereof, the connection is considered as a connection between holes which are not clearly aligned. An addition average value of an imaginary line set between hole centroids contained in an image may be set to be an inter-hole centroid distance which functions as a reference. An imaginary line which does not satisfy a predetermined reference, a pattern positioned at an end portion of the imaginary line, an area surrounded by the imaginary line or the pattern, and the like are distinguished from other imaginary lines and the like, distinguishment information thereof is registered or displayed in the display device. Thus, whether or not a material is suitable for patterning using a self-assembly phenomenon may be quantitatively evaluated.

Values are not required to be input to all of the setting areas 137, 138, and 139. An imaginary line, a pattern, or the like which meets specific conditions may be selected on the basis of an input to some areas.

After hole centroids are connected to each other with an imaginary line by a hole centroid connection unit 120, an evaluation calculation unit 121 for each hole calculates evaluation values of inclination of a hole (relative angle between an imaginary line and a reference line, and the like), the number of connections (the number of imaginary lines which performs appropriate connection or inappropriate connection, and the like), a connection angle (relative angle between adjacent imaginary lines, and the like), and an inter-hole distance (distance between hole centroids which are connected to each other with an imaginary line, and the like). A calculation method of the evaluation values relating to a plurality of holes will be described later.

The evaluation value calculation unit 121 for each hole calculates evaluation values, and then a grouping unit 122 of a hole distinguishes a pattern, an imaginary line, an area divided by the imaginary line, and the like so as to perform area division for each group in which holes are clearly aligned, for each of arrangement conditions of a plurality of holes, and/or to divide an area into an area in which holes are clearly aligned, and other areas. Evaluation values of the inclination of a hole, the number of connections, the connection angle, and the inter-hole distance at a boundary of each area in which holes are clearly aligned, are different from those in an area in which holes are clearly aligned. The inclination of a hole for each adjacent area is set to have a different value. In a case where evaluation values relating to a plurality of holes are set to have a different value, a boundary between holes is set, and an area is set. In a case where the relative angle of an imaginary line between adjacent hole centroids is not 60 degrees, a boundary of an area may be set between the holes.

In a case where the inter-hole distance has a value different from a value of the reference inter-hole centroid distance, a boundary of an area is set between the holes.

An area is divided by using the boundary. An evaluation value calculation unit 123 of an area calculates an evaluation value of an extent of areas obtained by division with the boundary, and an evaluation value of the number of holes in the area. Since it is considered that a plurality of areas obtained by division includes an area in which the number of holes is small (for example, an area in which one to several holes are provided), a threshold value relating to the size of an area or a threshold value relating to the number of holes included in the area is set in setting areas 134 and 135 of the GUI screen illustrated in FIG. 6. In the calculation device, an area which has a value more than the threshold value is selected. In this state, an area which has a value more than the threshold value, and in which holes are appropriately arranged as described above, or reversely, an area in which holes are not appropriately arranged is distinguished from other areas, and is displayed in the electron microscope image 127 as illustrated in FIG. 6. Examples of such an area include an area 128, an area 129, an area 130, and an area 131.

Specific processing details in the hole centroid calculation unit 119, the hole centroid connection unit 120, and the evaluation index calculation unit 121 of each hole will be described below.

Specific processing details in the hole centroid calculation unit 119 will be described with reference to FIGS. 2 and 3. FIG. 2 is a diagram illustrating a centroid calculation method which uses a contour-centroid scheme. FIG. 3 is a diagram illustrating a centroid calculation method which uses an area-centroid scheme. The contour-centroid scheme illustrated in FIG. 2 is a scheme in which a centroid is calculated in a case where each edge point (a1 to an) 202 of a hole 201 has mass. Coordinates of the contour-centroid are calculated by averaging coordinates of the edge points (Expression 203).

The area-centroid scheme illustrated in FIG. 3 is a scheme in which a centroid is calculated in a case where mass in a hole is uniform. A hole 301 is divided into triangles 303. Coordinates of the area-centroid are calculated from the sum of product by triangular centroid coordinates 304 and a triangular area, and a polygonal area (Expression 305). In the area-centroid scheme, considering that the size of the triangles 303 obtained by division is different from each other, when an average of the entirety of the figure is calculated from centroids of the triangles obtained by division, weighting with an area of the triangles is performed. Regardless of a method of division of the triangle, the area-centroid is constant.

FIG. 4 illustrates specific processing details in the hole centroid connection unit 120. In regard to a centroid 401 of a hole 400, other hole centroids 402, 403, 404, 405, 406, 407, 408, 409, 410, 411, and 412 are searched, and then, adjacent hole centroids are searched from among the other hole centroids. The searched adjacent hole centroids are connected to the centroid 401. Firstly, distances 413, 414, 415, 416, 417, 418, 419, 420, 421, 422, and 423 of other hole centroids 402, 403, 404, 405, 406, 407, 408, 409, 410, 411, and 412 from the hole centroid 401 are calculated.

A distance between two points is calculated from a square root of the sum of products of coordinates. At this time, if the distances are arranged in order of being short, the distances 413, 414, 415, 416, 417, and 418 of 402, 403, 404, 405, 406, and 407 are 6 from a side of being short, and are shorter than 419, 420, 421, 422, and 423. Six points from the side of being short are selected, and thus it is possible to specify hole centroids which are adjacent to each other. In the self-assembly of a hole, in a case where holes are clearly aligned, the number of adjacent holes may be set to 6, and the holes are aligned at an equal interval. Regarding a material and a pattern which are set as a target, many of alignment gaps are known in advance, and thus it is possible to specify adjacent holes even when hole centroids near to an alignment distance are selected. In a case where holes are not clearly aligned, the number of adjacent hole centroids may be 7 or 8. However, in this case, for example, a range in which an error can be allowed, a range in which an error is not allowed, or the like is input on the basis of setting conditions in the setting area 137, the setting area 138, and the setting area 139 of the GUI screen illustrated in FIG. 6, and thus filtering is performed.

Specific processing details of the evaluation index calculation unit 121 for each hole will be described with reference to FIG. 5. As described by using FIG. 4, after an adjacent hole centroid is specified, an angle relating to an imaginary line which is installed between centroids is calculated. Hole centroids adjacent to a centroid 502 of a hole 501 functioning as a target correspond to 503, 504, 505, 506, 507, and 508. Connection lines correspond to 509, 510, 511, 512, 513, and 514. An average of the inclination of the connection lines is defined as the inclination of a hole. Inclination reference lines 515, 516, 517, 518, 519, and 527 are set for the hole centroid 502 functioning as a target. The inclination reference lines cause the hole centroid to be set in a direction of being rotated around an origin point by 60 degrees. This direction is set to, for example, be rotated by 60 degrees, by using a vertical direction as a reference. Connection lines which have the smallest angle in a clockwise rotation and a counter-clockwise rotation, among the inclination reference lines 515, 516, 517, 518, 519, and 527 are obtained as connection lines which form a pair. In the example, regarding the inclination reference lines 515, 516, 517, 518, 519, and 527, the connection lines 509, 510, 511, 512, 513, and 514 function as counterparts. Angles 520, 521, 522, 523, 524, 525, and 526 are calculated by using the connection lines 509, 510, 511, 512, 513, and 514 which respectively correspond to the inclination reference lines 515, 516, 517, 518, 519, and 527. An average of the calculated angles is calculated by using an expression 528, and the calculated average is set as an inclination angle of a hole.

As described by using FIG. 5, in the example, an arrangement state of patterns which are arranged by self-assembly is quantified, and distribution indicating a state where patterns are arranged on a sample is evaluated. In FIG. 5, an example in which adjacent patterns are connected to each other by using an imaginary line is described. However, for example, as illustrated in FIG. 11, an imaginary line 1102 may be set between a centroid 1101 of a reference pattern, and a centroid 1103 of a pattern which is separated from the reference pattern by one piece, and a parameter such as an inter-centroid distance or an angle, which relates to arrangement of a plurality of centroids may be obtained. If a plurality of patterns is appropriately arranged, the length and the like of the imaginary line 1102 are close to an ideal value. Thus, the parameter is used as a determination index of whether or not patterns are appropriately formed.

Instead of the length of an imaginary line between holes, the angle information regarding the imaginary line, or the like, information of a closed-shape formed by using the imaginary line is quantified, and thus the arrangement state of patterns may be evaluated. For example, FIG. 14 illustrates a closed shape 1404 formed by three imaginary lines 1401, 1402, and 1403 which connect centroids of three adjacent patterns, to each other. It is also possible to evaluate the arrangement state of patterns by obtaining an area difference between the closed shape 1404 and an ideal shape 1405. In this case, for example, area additional value of areas 1406, 1407, and 1408, which function as a difference may be used as an index value. As the area difference becomes small, it is determined that patterns are arranged more appropriately. Thus, an area having an area difference which is equal to or less than a predetermined value is distinguished from other areas, at least one area is obtained, and thus it is possible to determine whether or not polymer functioning as a measurement target is suitable for patterning using the self-assembly phenomenon.

FIG. 15 is a diagram illustrating an example in which an area in which patterns are appropriately arranged, and an area in which patterns are not appropriately formed are distinguished from each other and are displayed in an electron microscope image 1501. An area 1502 in which patterns are not appropriately formed is an area in which patterns formed therein are formed so as to be deviated, and which is distinguished from other areas by the above-described determination index such as angle information regarding the inter-centroid distance and the imaginary line. Such distinguishment is performed, and thus even when an extent of an area in which patterns are appropriately arranged or an extent of an area in which patterns are not appropriately formed is obtained, determination whether or not polymer functioning as a measurement target is suitable for patterning using the self-assembly phenomenon may be performed.

FIGS. 16 and 17 are diagrams illustrating examples in which a pattern which is not appropriately formed, or an imaginary line obtained by setting the pattern as a base point is distinguished from other patterns or other imaginary line, and is displayed. FIG. 16 illustrates an example in which an imaginary line 1601 of which the length or the angle does not satisfy the predetermined condition is distinguished from an imaginary line 1602 of which the length or the angle satisfies the predetermined condition, and is displayed. FIG. 17 illustrates an example in which a pattern 1702 which does not satisfy predetermined arrangement conditions is distinguished from other patterns, and is displayed. In this manner, an imaginary line or a pattern may be distinguished and the polymer may be evaluated by using ratio and the like of both values thereof.

Figure 13B:
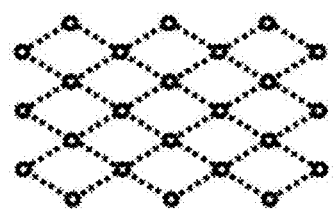
Figure 13C:
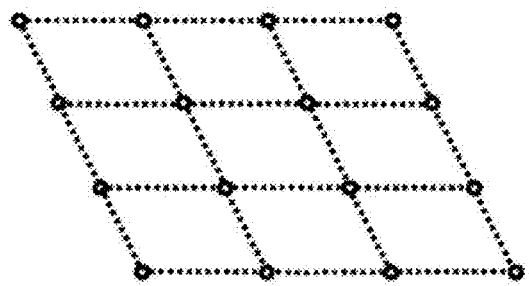

Hitherto, an example of a sample in which 6 patterns are arranged around one pattern which is set to be appropriately formed, and the 6 patterns are arranged so as to have a regular hexagonal shape is described. However, for example, as illustrated in FIG. 13(*a*), a sample in which patterns are arranged so as to have a rectangular shape, a sample in which patterns are arranged so as to be rhomboid as illustrated in FIG. 13(*b*), or a sample in which patterns are arranged so as to have a parallelogram shape as illustrated in FIG. 13(*c*) is set as a measurement target, and evaluation may be performed on the basis of arrangement determination of the above-described imaginary line or pattern.

EXAMPLE 2

In the example, an example in which patterns which are arranged by the self-assembly are evaluated on the basis of an image acquired by the electron microscope will be mainly described. The extent of an area (below referred to as a grain area) in which alignment by the self-assembly is performed is relatively wide, and thus the entirety of the grain area is not viewed in a field of view when an image having high magnification, as obtained by the electron microscope, is observed narrowly. In a case of an image obtained by acquiring at low magnification in order to widen the field of view, the number of pixels to a hole diameter is reduced, and thus a signal-to-noise ratio (S/H) may be lowered and detection of a hole position itself may be not possible. In an example which will be described below, an example in which various parameters required for measurement can be set, and thus various grain areas, and a hole diameter are allowed to be measured will be described.

A first method is a method in which a hole position at the low magnification is detected by using a pitch and a hole diameter which have been measured at the high magnification. In this method, sample images are acquired at the high magnification and the low magnification, at the same location or the neighboring location on a wafer. FIG. 7 illustrates an example of data allowed to be acquired during measurement at the high magnification. FIG. 8 illustrates an example of a parameter details setting screen. At the high magnification, since a narrow field of view is scanned with an electron beam, it is possible to acquire an image having good S/N for a short time, and to measure a fine hole diameter or a fine pitch between holes with high accuracy.

In the example of the data output in FIG. 7, the following data may be set as an output: the number of all holes in a screen; the number of normal holes which have high circularity and will be described later; the number of holes which have low circularity and are considered as a defect; an average diameter of normal holes and a value (3sigma) obtained by trebling the standard deviation thereof; an average value of all pitches between normal holes and a value obtained by trebling the standard deviation thereof; and an average of circularity of all holes and a value obtained by trebling the standard deviation thereof. The circularity is calculated by using Expression 1.

$$(\text{circularity}) = 4\pi \times (\text{hole area})/(\text{hole contour line length})^2 \quad \text{Expression 1}$$

Regarding the number of defective holes, in a case where the circularity is smaller than a threshold value of Roundness in FIG. 8 the hole is set as a defective hole. The number of normal holes is set to be obtained by subtracting the number of defective holes from the number of all holes.

A threshold value allowed to be set in the details setting screen in FIG. 8 will be described. A gray-scale threshold value (Gray Level) is used when a hole contour is determined. In a searching range of a pitch (Pitch Search Area), the neighboring holes are searched in a range set for a pitch of a design value (Design Value) input in FIG. 7. Similarly, in a hole diameter searching range (Diameter Search Area), a hole diameter for performing detection as a hole is designated.

The above-descriptions are used for the example of measurement at the high magnification. Since extraction of a grain area is the main purpose at the low magnification, a hole diameter, the circularity, or the like is not output. FIG. 9 illustrates an example of data allowed to be acquired during measurement at the low magnification. FIG. 10 illustrates an example of a parameter details setting screen relating to measurement of a grain area, in the example of data output in FIG. 9, the number of all holes in the screen (Number (Total)), the number of normal holes of which the number of connections with the neighboring hole is 6 (Number (Normal Hole)), the number of holes which are considered as a defect, of which the number of connections with the neighboring hole is not 6 (Number (Defect Hole)), the number of grouped grain areas (Number (Grain Area)), an average hole number in the grouped grain area (Average (Hole Number)), and the maximum value thereof (Maximum (Hole Number)), an average value of all pitches and a value obtained by trebling the standard deviation thereof are provided.

A threshold value allowed to be set in the details setting screen in FIG. 10 will be described. A gray-scale threshold value (Gray Level) is used when a hole contour is determined. In a searching range of a pitch (Pitch Search Area), the neighboring holes are searched in a range set for a pitch (Pitch) of a design value (Design Value) input in FIG. 9. Regarding a threshold value of the number of holes (Hole Number), an upper limit and a lower limit of the number of estimates obtained by the following Expression 2 may be set by using the pitch (Pitch) of the input design value and the size of a field of view when an image is acquired.

$$(\text{number of estimated holes}) = 2 \times (\text{vertical width of field of view}) \times (\text{horizontal width of field of view})/(\sqrt{3} \times (\text{pitch})^2) \quad \text{Expression 2}$$

In a case where automatic performing (Auto) is selected in FIG. 10, a value set by using the design value is not calculated, but an average pitch and an average hole diameter which are measured at the high magnification, a threshold value when a hole contour is extracted by using the number of holes, a searching range of a pitch, and an upper limit value and an lower limit value of the number of holes are automatically calculated. The minimum number of grains is not automatically determined.

As a method of detecting a hole position at the low magnification cation by using only an image at the low magnification, a pitch from a sample image is calculated, in addition to a method of measuring by using the input design value. In order to calculate the pitch, a method of creating an integrating profile for an image after the Fourier transform, in an angular direction, and detecting a peak thereof, or a method of creating a self-correlation image, creating an integrating profile in the angular direction, and detecting a peak thereof, and the like are used.

EXAMPLE 3

In the grouping unit 122 of a hole, grouping may be performed without setting an area between holes, as described above. A method of performing grouping from the hole inclination and the number of connections which are calculated in FIG. 5 and are attributes of each hole, and from centroid coordinates of holes, which are obtained by the hole centroid calculation unit 119 will be described.

Firstly, holes of which the number of connections is not 6 are filtered. At this time, a filtered hole is stored as a defective hole. Then, classification is performed by using the hole inclination and the centroid coordinate. For the classification, a method in which an area is divided by the same hole inclination with a dividing and integrating method, or a method in which a histogram for each hole inclination angle is created, a multi-peak trough portion is divided, and then a hole group having centroid coordinates close to each other is subjected to labeling processing, and the like are used. Then, the number of holes in each area may be counted, and the extent of each area may be calculated from a value of the pitch input or calculated in Examples 1, 2, and 3, by using Expression 3.

$$(\text{extent of area}) = (\text{number of holes}) \times \sqrt{3}/2 \times (2 \text{ sets of average pitches}) \quad \text{Expression 3}$$

EXAMPLE 4

FIG. 18 is a diagram illustrating an example in which distinguishment information is superimposed on a DSA pattern image having the high magnification, in accordance with the features of a pattern. A pattern 1801 is a normal pattern, and a circular figure similar to the pattern is superimposed on the pattern 1801. A pattern 1802 is a pattern which does not satisfy the predetermined conditions, and the shape of the pattern is largely different from a circular shape. Thus, distinguishment information different from that for a circular shape is superimposed on the pattern 1802. It is possible to visually recognize a range of patterns which are appropriately formed, and an tendency thereof by performing such distribution displaying.

FIG. 19 is a diagram illustrating an example in which distinguishment information is superimposed on a DSA pattern image having the low magnification, in accordance with the features of a pattern. In FIG. 19, an area in which features of patterns are largely changed is selectively displayed, particularly among low magnification images. A pattern surrounded by a quadrangle is a pattern which satisfies predetermined conditions (relative relationship and the like to adjacent patterns). A pattern having an attached mark of x is a pattern determined that the predetermined conditions are not satisfied. In this manner, the distinguishment information is superimposed on the low magnification cation image in accordance with the features of each pattern, and is displayed, and thus it is possible to distinguish between an area in which patterns are appropriately formed, and an area in which patterns are not appropriately formed, and to determine whether composition of polymer is good or bad. In the example of FIG. 19, it is understood that the distinguishment information in accordance with the features of a pattern is added onto an SEM image 1901 and an area in which the predetermined conditions are not satisfied is interposed between an area 1902 and an area 1903. It is possible to confirm the size of an effective use area of polymer by performing such display, and as a result, it is possible to determine whether composition of polymer is good or bad.

The invention claimed is:

1. A pattern measurement device comprising:
    a calculation device that measures a dimension between patterns formed in a sample, by using data which is obtained by irradiating the sample with a beam,
    wherein
    the calculation device
    obtains centroids of a plurality of patterns contained in the data;
    obtains at least one of an inter-centroid distance of the plurality of patterns, angle information of imaginary lines which link the plurality of centroids to each other, and area information of a closed shape formed by the imaginary lines; and
    distinguishes at least one of a pattern which meets a specific condition, an area including the pattern which meets the specific condition, and an imaginary line between patterns meeting the specific condition, from at least one of a pattern different from the pattern which meets the specific condition, an area other than the area including the pattern which meets the specific condition, and an imaginary line between patterns other than the patterns meeting the specific condition, on the basis of at least one of the inter-centroid distance, the angle information, and the area information which have been obtained, or
    calculates information regarding at least one of the number of patterns meeting the specific condition, a size of the area including the patterns which meet the specific condition, and the number of imaginary lines between the patterns meeting specific condition.

2. The pattern measurement device according to claim 1, wherein
    the pattern is formed by self-assembly of molecules.

3. The pattern measurement device according to claim 1, wherein
    the calculation device obtains the centroid on the basis of an edge or contour line information of the pattern.

4. The pattern measurement device according to claim 1, wherein
    the calculation device obtains at least one of a relative angle between the imaginary lines and a reference line functioning as a reference, and a relative angle between the imaginary lines, as the angle information.

5. The pattern measurement device according to claim 1, wherein
    the calculation device obtains an area difference between a reference figure and the closed shape formed by the imaginary lines.

6. The pattern measurement device according to claim 1, further comprising:
    a display device that distinguishes and displays at least one of the pattern meeting the specific condition, the area including the pattern which meet the specific condition, and the imaginary line between the patterns meeting the specific condition, from at least one of the pattern other than the pattern meeting the specific condition, the area different from the area including the pattern which meet the specific condition, and the imaginary line between the patterns other than the patterns meeting the specific condition.

7. The pattern measurement device according to claim 1, further comprising:
    a display device that displays at least one of the inter-centroid distance of the plurality of patterns, the angle information of imaginary lines which link the plurality of centroids, and the area information of the closed shape formed by the imaginary lines.

8. The pattern measurement device according to claim 1, further comprising:
    a display device that displays distribution of at least one of the inter-centroid distance of the plurality of patterns, the angle information of imaginary lines which link the plurality of centroids, and the area information of the closed shape formed by the imaginary lines, in accordance with a value of the at least one.

9. The pattern measurement device according to claim 1, further comprising:
    a display device that distinguishes and displays at least one of the pattern meeting the specific condition, the area including the pattern meeting the specific condition, and the imaginary line between the patterns meeting specific condition, from at least one of the pattern different from the pattern meeting the specific condition, the area other than the area including the pattern meeting the specific condition, and the imaginary line between the patterns other than the patterns meeting the specific condition.

10. The pattern measurement device according to claim 1, wherein
    the calculation device performs grouping of at least one of the patterns meeting specific condition, and the imaginary lines between the patterns meeting specific condition.

11. A non-transitory computer-readable medium storing a program causing a computer to measure dimensions between patterns formed in a sample, by using data which is obtained by irradiating the sample with a beam, wherein the program causes the computer to:

obtain centroids of a plurality of patterns contained in the data;

obtain at least one of an inter-centroid distance of the plurality of patterns, angle information of imaginary lines which link the plurality of centroids to each other, and area information of a closed shape formed by the imaginary lines; and distinguish at least one of a pattern which meets a specific condition, an area including the pattern which meets the specific condition, and an imaginary line between patterns meeting the specific condition, from at least one of a pattern different from the pattern which meets the specific condition, an area other than the area including the pattern which meets the specific condition, and an imaginary line between patterns other than the patterns meeting the specific condition, on the basis of at least one of the inter-centroid distance, the angle information, and the area information which have been obtained, or calculate information regarding at least one of the number of patterns meeting the specific condition, a size of the area including the pattern which meet the specific condition, and the number of imaginary lines between the patterns meeting the specific condition.

* * * * *